United States Patent [19]

Knight, Jr.

[11] 4,278,661

[45] Jul. 14, 1981

[54] PURIFICATION OF INTERFERON

[75] Inventor: Ernest Knight, Jr., Wilmington, Del.

[73] Assignee: E. I. Du Pont de Nemours and Company, Wilmington, Del.

[21] Appl. No.: 84,632

[22] Filed: Oct. 12, 1979

[51] Int. Cl.[3] .............................................. A61K 45/02

[52] U.S. Cl. ....................................... 424/85; 435/811

[58] Field of Search ...................... 424/85; 260/112 R; 435/68, 811

[56] References Cited

U.S. PATENT DOCUMENTS 4,172,071 10/1979 De Maeyer et al. ............ 260/112 R

OTHER PUBLICATIONS

Jankowski, W., et al., Biochemistry, vol. 15, pp. 5182-5187, (1976).

Bollin, E., et al., Preparative Biochemistry, vol. 8, pp. 259-274, (1978).

Erickson, J., et al., Interferon Scientific Memoranda, Mar. 1979.

Erickson, J., et al., Analytical Biochemistry, vol. 98, pp. 214-218, (1979).

Osario, T., et al., Proc. Soc. Exp. Biol. Med., vol. 153, pp. 484-489, (1976).

Maeyer-Guignard et al., C. R. Acad. Sc. Paris, vol. 283, pp. 709-711, (1976).

Davey, M., et al., Biochemistry, vol. 15, pp. 5182-5187, (1976).

Sulkowski et al., J. Biol. Chem., vol. 251, pp. 5381-5385, (1976).

Stewart, W., Editor, CRC Press, Inc., Cleveland, Ohio, "Interferon," pp. 49-72, (1977).

"Blue Sepharose CL-6B For Affinity Chromatography," Sep. 1976, Pharmacia Fine Chemicals, publisher.

*Primary Examiner*—Delbert R. Phillips
*Assistant Examiner*—Blondel Hazel
*Attorney, Agent, or Firm*—C. Harold Herr; James A. Costello

[57] ABSTRACT

Human interferons produced in the absence of added serum or sera can be purified to greater than 95% protein purity by adsorption on immobilized Cibacron Blue F3G-A and eluting the interferon adsorbed on the Cibacron Blue F3G-A with ethylene glycol in an aqueous buffer solution. The purified interferon in solution can be converted to interferon of uniform molecular weight by heating the interferon solution in the presence of an organic thiol compound.

7 Claims, No Drawings

PURIFICATION OF INTERFERON

TECHNICAL FIELD

This invention relates to a process for the purification of serum-free human interferons by chromatography on immobilized Cibacron Blue F3G-A.

BACKGROUND ART

Purification and characterization of interferons, both human and animal, have been studied extensively over the past two decades, and the subject has been reviewed recently by Stewart in "Interferons and Their Actions," William E. Stewart II Editor, CRC Press, Inc., Cleveland, Ohio, 1977, pages 49–72. Jankowski et al, Biochemistry 15, 5182–5187 (1976), studied the binding of human interferons to Blue Dextran, i.e., dextran substituted with Cibacron Blue F3G-A, immobilized on cyanogen bromide-activated agarose. Both human fibroblast and leukocyte interferons bind to Cibacron Blue F3G-A under appropriate solvent conditions. This binding results in a significant purification of fibroblast interferon and reveals the molecular heterogeneity of human leukocyte interferon. Fibroblast interferon is reportedly eluted from the column with ethylene glycol solution, e.g., 50%, to give an 800-fold purification with a 95% recovery of activity. Similar purifications to those previously reported by Davey et al, Biochemistry 15, 704 (1976) on concanavalin A-agarose and by Sulkowski et al, J. Biol. Chem. 251, 5381 (1976) on L-tryptophan-agarose were obtained. However, the fibroblast interferon preparations employed as starting materials usually contained fetal calf serum.

Bollin et al, Preparative Biochemistry, 8, 259–274 (1978), studied binding of mouse, hamster, rabbit, horse and human fibroblast interferons on immobilized Cibacron Blue F3G-A under appropriate solvent conditions. Of the three forms of immobilized ligand investigated, interferons were most tightly bound to Blue Sepharose CL-6B, and human fibroblast interferon was displaced from the sorbant only upon inclusion of ethylene glycol in the eluant.

Erickson et al, Interferon Scientific Memoranda, March, 1979, disclose the purification of human leukocyte and human lymphoblastoid interferons in albumin-containing preparations by adsorption chromatography on Blue Sepharose.

In none of the aforementioned references was serum-free interferon employed.

DISCLOSURE OF INVENTION

The present invention comprises a process for the purification of serum-free human interferons to greater than 95% protein purity which comprises:

(a) contacting an aqueous solution of serum-free human interferon with immobilized Cibacron Blue F3G-A, whereupon the interferon is adsorbed on the Cibacron Blue F3G-A;

(b) eluting the adsorbed interferon by washing the immobilized Cibacron Blue F3G-A with an eluting solvent to obtain a solution of purified interferon of greater than 95% protein purity.

Optionally, the resulting purified interferon can be converted to interferon of uniform molecular weight by reaction of the purified interferon with an aqueous solution of an organic thiol compound.

The process of the invention employs a serum-free human interferon in contrast with earlier described purification processes which used interferon contaminated with protein-containing serum. By the term "serum-free human interferon" is meant interferon produced in the absence of added serum or sera. The addition of serum proteins enhances the yield of interferon, but the added proteins must be removed in subsequent purification. Removal of serum proteins may require numerous steps with excessive loss of interferon. Furthermore, use of serum-free interferon produces a higher purity product with avoidance of foreign protein antigens which give undesired febrile response in patients.

The process of the invention can be used to purify any of the human interferons including human fibroblast interferon, human leukocyte interferon, and human lymphoblastoid interferon, but it is preferred to employ human fibroblast interferon.

The adsorbant of the process, Cibacron Blue F3G-A, can be immobilized on any of a variety of commonly used supports. Such supported adsorbants include coupling of the dye via the amino group of the anthraquinone moiety to cyanogen bromide activated agarose to give Cibacron Blue F3G-A-Sepharose 4B; coupling of the dye to the cross-linked agarose gel Sepharose CL-6B by the triazine coupling method, described by Böhme et al, J. Chromatogr., 69, 209–214 (1972), via an ether linkage to give Blue Sepharose CL-6B; and coupling of Blue Dextran (Cibacron Blue F3G-A-dextran) to cyanogen bromide activated agarose to give Blue Dextran-Sepharose 4B. Several such adsorbants may be purchased from Pharmacia, Inc.

It is preferred to employ commercially available Blue Sepharose CL-6B because of its highly effective binding action.

The adsorption step (a) of the process is conveniently carried out at temperatures of from about 15° to about 30° C., preferably about room temperature, by passing a solution of impure interferon at, preferably, atmospheric pressure through a chromatographic column packed with immobilized Cibacron Blue F3G-A. In this way essentially complete adsorption of the interferon is achieved. Alternatively, the impure interferon can be mixed with immobilized Cibacron Blue F3G-A in a batch process.

The elution step (b) of the process is carried out with a solvent suitable for eluting purified interferon but which is not effective for eluting more tightly bound proteinaceous impurities, e.g., aqueous sodium chloride solution or aqueous ethylene glycol. The chromatographic column may be washed with column buffer solution to remove unbound or loosely bound proteinaceous impurities before carrying out the interferon-eluting step. With human fibroblast interferon adsorbed on Blue Sepharose CL-6B, elution is preferably carried out with about 35 to about 45 weight percent of ethylene glycol in an aqueous buffer solution at about room temperature.

Although the process of the invention can be carried out with a single pass through the immobilized Cibacron Blue F3G-A column, it is sometimes preferable to employ a relatively large column followed by a relatively small column to aid in concentrating the volume of the purified interferon solution.

Purity of the purified interferon is usually determined by electrophoresis through poly(acrylamide) gel in denaturing conditions. For example, interferon may be denatured in sodium dodecyl sulfate (SDS) and subjected to electrophoresis using buffers containing, preferably, 0.1% SDS; see U. K. Laemmli, Nature, 227, pages 680–685 (1970), for description of a suitable buffer system.

When serum-free human fibroblast interferon is purified by the process of this invention, the purified product is obtained as a mixture of "monomer", molecular weight about 20,000, and "dimer", molecular weight about 40,000. Conversion of the interferon dimer to monomer can be achieved by contacting the interferon solution with an organic thiol compound, preferably thioglycolic acid, β-mercaptoethanol or dithiothreitol (Cleland's reagent), preferably about 0.02 molar, at a temperature of, preferably, about 80°–90° C. for about 1–5 minutes. Although both "monomer" and "dimer" show biological activity, it is desirable from an activity viewpoint to have all the interferon activity in a single molecular weight fraction.

The conversion is preferably performed by heating to a temperature of from about 80° to 90° C. the mixture of "monomer" and "dimer" with a 0.1–1% aqueous solution of SDS containing about 0.02 molar concentration of the organic thiol compound. The period of heating may vary over a wide range but preferably is about 1 to 5 minutes. The quantity of the organic thiol compound employed is preferably kept to a minimum because of its odor.

The following are illustrative examples of the invention in which all parts and percentages are by weight and all degrees are Celsius unless otherwise specified.

EXAMPLE 1

Human fibroblast interferon was produced by human diploid fibroblast cells in serum-free medium as previously described (E. Knight, Jr. (1976) Proc. Natl. Acad. Sci. USA 73, 520–523). Approximately 15 liters of crude interferon were collected for purification.

A 4 cm×10 cm column of Blue Sepharose CL-6B was prepared and equilibrated overnight with a buffer of 0.02 M sodium phosphate, pH 7.2, containing 1 M sodium chloride. Crude interferon solution, about 15 l was made 1 M in sodium chloride and passed through the column at room temperature and atmospheric pressure. The column was washed with about 600 ml of column buffer to remove unbound protein, about 95–99% of the total initial protein. Interferon was eluted from the column with an aqueous solution, 0.02 M in sodium phosphate, pH 7.2, 1 M in sodium chloride, and 50% ethylene glycol. Biologically active material was eluted with this solution in a volume of 150 ml of solution.

The solution containing the biologically active material was concentrated and further purified by passage through a small column, 0.8 cm×6 cm, of Blue Sepharose CL-6B, initially equilibrated with a buffer of 0.02 M sodium phosphate, pH 7.2, which was 2 M in sodium chloride. The 150 ml eluant from the large column was diluted with 1.5 volumes of column buffer and passed through this small column at room temperature and atmospheric pressure. The column was eluted with 10 ml of column buffer which contained 30% ethylene glycol, and 1-ml fractions were collected separately. Subsequently, the column was sequentially eluted with two 10-ml portions of column buffer, the first portion containing 40% ethylene glycol and the second portion containing 50% ethylene glycol. Small portions of interferon were found in the 30% and 50% ethylene glycol eluants, but the majority of the product was eluted in the 40% ethylene glycol fraction.

Interferon impurity was determined by electrophoresis through poly(acrylamide) gel slabs, 0.75 mm thick, in denaturing conditions. Denaturing was achieved in SDS, and electrophoresis was employed using buffers which contained SDS, as described by U. K. Laemmli, Nature, 227, 680–685 (1970). Proteins were separated on the basis of size, and were observed as discrete bands after staining with Coomassie Blue. Protein eluted in the 40% ethylene glycol fraction contained only one major protein, interferon, and it was estimated to comprise greater than 95% of the protein in this fraction.

The results of the experiment are summarized in Table I.

TABLE I

PURIFICATION OF HUMAN FIBROBLAST INTERFERON ON BLUE SEPHAROSE CL-6B

| Fraction | Percent Recovery of Original Interferon Biological Activity[1] | Purity of Interferon, % |
|---|---|---|
| Initial crude Interferon | 100 | 0.02 |
| Blue Sepharose col., 4 × 10 cm, 50% ethylene glycol | 75 | 20 |
| Blue Sepharose col., 0.8 × 6 cm 30% ethylene glycol | 15 | 10 |
| Blue Sepharose col., 0.8 × 6 cm, 40% ethylene glycol | 50 | >95 |
| Blue Sepharose col., 0.8 × 6 cm, 50% ethylene glycol | 10 | 75 |

[1] Interferon activity was determined on human fibroblast cells in culture by inhibition of virus induced cytopathic effect; see Armstrong, J. A. (1971) Appl. Microbiol. 21, 723–725. Vesicular stomatitis virus was the challenge virus.

EXAMPLE 2

Example 1 was repeated and an interferon-containing fraction, eluted from the 0.8×6 cm column of Blue Sepharose CL-6B, was analyzed for molecular weight by mobility using poly(acrylamide) gel electrophoresis. Molecular weight standards of 13,000, 23,000 and 44,000 were employed. The product was found to consist of interferon "monomer", molecular weight about 20,000, and "dimer", molecular weight of about 40,000. The interferon-containing fraction was heated in the presence of 0.1% of SDS and a 0.02 M concentration of thioglycolic acid for a period of 2 minutes at 80°–90° C. Molecular weight analysis of the product showed that dimer had been converted to monomer.

BEST MODE

The best mode contemplated by the applicant for carrying out the invention is described in Examples 1 and 2.

INDUSTRIAL APPLICABILITY

The process of this invention can be used to purify large amounts of human interferons without resorting to other purification steps such as electrophoresis which could cause modification and/or contamination of the interferon. Interferon for large scale therapeutic use, both antiviral and antitumor, must be pure. The purified product is suitable for protein sequence studies. Such studies may yield peptide fragments with antiviral and antitumor utility in man.

I claim:

1. In a process for purifying biologically active serum-free human interferon comprising contacting an aqueous solution of impure serum-free human interferon with immobilized Cibacron Blue F3G-A, adsorbing the interferon on the Cibacron Blue F3G-A, and eluting the adsorbed interferon by washing the Cibacron Blue F3G-A with an eluting solvent to obtain a solution of purified interferon, the improvement which comprises:

(i) employing, as eluting solvent, an aqueous buffer solution containing 35 to 45 percent of ethylene glycol, thereby obtaining interferon of greater than 95% purity, (ii) obtaining the purified interferon as a mixture of monomer and dimer, and (iii) contacting the purified interferon mixture with an organic thiol compound to convert dimer to monomer, whereby all interferon activity resides in the monomer molecular weight fraction.

2. The process of claim 1 in which the serum-free human interferon is fibroblast interferon.

3. The process of claim 1 in which the immobilized Cibacron Blue F3G-A is Blue Sepharose CL-6B.

4. The process of claim 1 in which the aqueous solution of impure serum-free human interferon is passed through a chromatographic column packed with Blue Sepharose CL-6B at atmospheric pressure and a temperature of from about 15° to 30° C.

5. The process of claim 4 in which the solution of purified interferon is passed through a second chromatographic column packed with Blue Sepharose CL-6B to concentrate the volume of the purified interferon solution.

6. The process of claim 1 in which the organic thiol compound is selected from the class consisting of thioglycolic acid, β-mercaptoethanol and dithiothreitol.

7. The process of claim 1 in which the solution of purified interferon is brought into contact with sodium dodecyl sulfate as a 0.1 to 1% aqueous solution, at a temperature of from about 80° to 90° C. for a period of from 1 to 5 minutes.

* * * * *